(12) United States Patent
Cude

(10) Patent No.: US 7,819,845 B2
(45) Date of Patent: Oct. 26, 2010

(54) SYRINGE PLUNGER JACKET WITH EXPANDABLE SEAL

(75) Inventor: J. Michael Cude, College Grove, TN (US)

(73) Assignee: Coeur, Inc., Lebanon, TN (US)

( * ) Notice: Subject to any disclaimer, the term of this patent is extended or adjusted under 35 U.S.C. 154(b) by 287 days.

(21) Appl. No.: 11/760,040

(22) Filed: Jun. 8, 2007

(65) Prior Publication Data

US 2007/0233002 A1    Oct. 4, 2007

Related U.S. Application Data

(63) Continuation-in-part of application No. 11/279,644, filed on Apr. 13, 2006.

(60) Provisional application No. 60/594,496, filed on Apr. 13, 2005.

(51) Int. Cl.
*A61M 5/00* (2006.01)

(52) U.S. Cl. .................. 604/181; 604/187; 604/151; 604/152; 604/153; 604/154; 604/155; 604/212; 604/213; 604/214; 604/215; 604/216; 604/217; 604/128; 600/432

(58) Field of Classification Search ............... 604/181, 604/187, 151–155, 212–217, 128; 600/432
See application file for complete search history.

(56) References Cited

U.S. PATENT DOCUMENTS

| | | | |
|---|---|---|---|
| 3,147,753 A * | 9/1964 | Nogier et al. ............... 604/222 |
| 3,623,474 A * | 11/1971 | Heilman et al. ............ 600/432 |
| 3,631,847 A * | 1/1972 | Hobbs, II .................... 600/432 |
| 3,890,956 A | 6/1975 | Moorehead et al. |
| 4,041,934 A * | 8/1977 | Genese ....................... 600/576 |
| 4,201,209 A | 5/1980 | LeVeen et al. |
| 4,214,507 A | 7/1980 | Hock et al. |
| 4,266,559 A * | 5/1981 | Akhavi ....................... 600/579 |
| 4,340,067 A | 7/1982 | Rattenborg |
| 4,411,275 A | 10/1983 | Raitto |
| 4,704,105 A | 11/1987 | Adorjan et al. |

(Continued)

FOREIGN PATENT DOCUMENTS

WO    2006109272 A2    10/2006

OTHER PUBLICATIONS

Office Action from U.S. Appl. No. 11/279,644—Aug. 12, 2008—13 pages.

(Continued)

*Primary Examiner*—Nicholas D Lucchesi
*Assistant Examiner*—Scott Medway
(74) *Attorney, Agent, or Firm*—Hahn, Loeser & Parks, LLP

(57) ABSTRACT

A syringe plunger/jacket assembly may comprise a flexible jacket attached to a rigid plunger. The jacket may comprise at least two sealing rings (front and rear) that prevent fluid from leaking out of the rear of the barrel during injection of fluid from the syringe. The rear sealing ring may or may not contact or seal the interior surface of the syringe barrel in an unloaded state. In the loaded state, when force is applied in the direction of the forward discharge end of the syringe, pressure is created on the jacket. This condition causes the rear seal to expand and contact and/or seal the interior surface of the syringe barrel.

8 Claims, 3 Drawing Sheets

U.S. PATENT DOCUMENTS

| | | | |
|---|---|---|---|
| 4,874,372 A | 10/1989 | McArthur et al. | |
| 5,314,416 A * | 5/1994 | Lewis et al. | 604/219 |
| 5,383,864 A | 1/1995 | van den Heuvel | |
| 5,397,313 A | 3/1995 | Gross | |
| 5,735,825 A | 4/1998 | Stevens et al. | |
| 5,788,677 A * | 8/1998 | Botich et al. | 604/195 |
| 5,868,710 A | 2/1999 | Battiato et al. | |
| 5,902,276 A | 5/1999 | Namey | |
| 5,925,022 A | 7/1999 | Battiato et al. | |
| 6,004,292 A | 12/1999 | Battiato et al. | |
| 6,017,330 A | 1/2000 | Hitchins et al. | |
| 6,159,183 A | 12/2000 | Neer et al. | |
| 6,183,441 B1 * | 2/2001 | Kriesel et al. | 604/132 |
| 6,224,577 B1 | 5/2001 | Dedola et al. | |
| 6,254,572 B1 | 7/2001 | Knipfer et al. | |
| 6,447,487 B1 * | 9/2002 | Cane' | 604/181 |
| 2004/0116854 A1 * | 6/2004 | Abulhaj et al. | 604/110 |
| 2004/0215149 A1 * | 10/2004 | Hjertman | 604/187 |
| 2004/0254543 A1 | 12/2004 | Griffiths | |
| 2005/0033237 A1 | 2/2005 | Fentress et al. | |
| 2005/0224730 A1 | 10/2005 | Fago et al. | |
| 2007/0088270 A1 | 4/2007 | Cude | |
| 2007/0179449 A1 * | 8/2007 | Berman et al. | 604/187 |

OTHER PUBLICATIONS

Office Action from U.S. Appl. No. 11/279,644—May 4, 2009—21 pages.

* cited by examiner

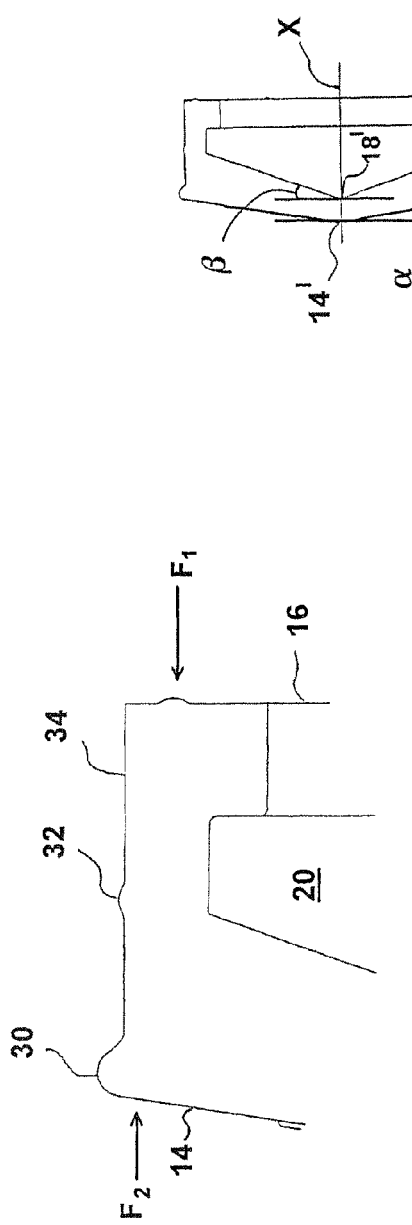
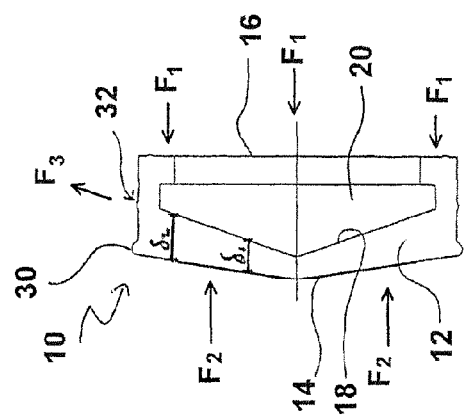
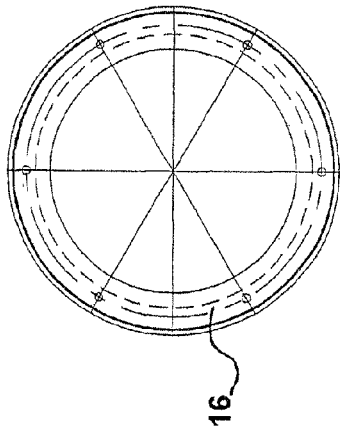
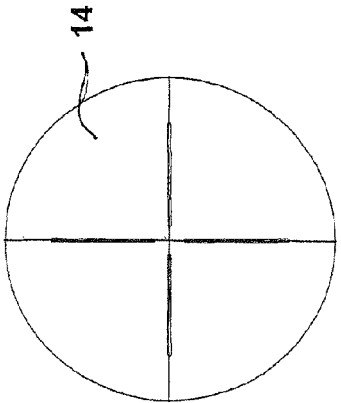
FIG. 1
FIG. 2
FIG. 3
FIG. 4
FIG. 5

SYRINGE PLUNGER JACKET WITH EXPANDABLE SEAL

This Continuation-in-part patent application claims priority to U.S. utility patent application Ser. No. 11/279,644 filed on Apr. 13, 2006, which claims priority to U.S. provisional patent application Ser. No. 60/594,496 filed on Apr. 13, 2005, both of which are incorporated herein in its entirety.

TECHNICAL FIELD

The present invention relates to syringes used in conjunction with power injectors. More particularly, the present invention relates to syringe plunger jackets having at least one expandable seal.

BACKGROUND OF THE INVENTION

Power injectors for injecting fluid into animals are well known in the art. A typical power injector comprises an injector head, having a syringe mount, and a drive ram reciprocally mounted thereon. This syringe is mounted to the injector in either a breach-load manner or a front load manner. The syringe can either be pre-filled or empty, i.e., the user must first draw contrast into the syringe before injecting fluid.

Syringes for power injectors are also well known in the art. As stated in the preceding paragraph, the syringe can be a front load type, in which the rear end of the syringe is inserted into the injector to attach the syringe to the injector. Additionally, the syringe could be breach loaded, such that, for example, a face plate of the injector is rotatable and the syringe is loaded through the rear the face plate, front end first.

A drive ram of the injector may attach to the plunger of the syringe to move the plunger forward relative to the syringe, to expel fluid from the discharge end of the syringe. In typical injection procedures, the pressure generated by the forward translation of the plunger can range from about 100 psi to 1200 psi. To ensure that contrast fluid from the syringe does not leak past the plunger, plunger assemblies typically comprise at least two (2) integral sealing rings that contact the inside surface of a syringe barrel. Typically, the forward-most sealing ring performs the majority of the sealing process, and the rearward most sealing ring is a backup safety seal in case the forward-most ring fails.

One aspect of syringe plungers having two (2) seal sealing rings relates to sterilization of the area between the two (2) sealing rings, once installed in the syringe. With most materials, it is difficult for a sterilization gas to reach the area between the two (2) sealing rings. Accordingly, there is a need for a syringe jacket (seal) that overcomes the deficiencies in the prior art. The embodiments of the present invention overcome the difficult-to-sterilize space between the two seals when the plunger is installed in the syringe.

Another aspect of syringe plungers relates to how the plunger jacket moves against the interior surface of the syringe barrel during expulsion of fluid from the syringe. Some materials, from which the plunger jacket is constructed, have greater tactile resistance than other materials. When driven forward through the barrel, plunger jackets made from such materials may chatter or intermittently stick to the side walls, which may introduce noise into CT scanning systems utilizing the power injector and syringe. While other materials may glide easier against the surface of the barrel, such materials may not have sufficient tensile strength to maintain a seal against certain pressures during use. What is needed is a plunger that smoothly and evenly travels down the barrel without chatter but also seals against the operating pressures of the syringe. The embodiments of the present invention obviate the aforementioned problems.

SUMMARY OF THE INVENTION

A syringe plunger/jacket assembly may comprise a flexible jacket attached to a rigid plunger. The jacket may comprise at least two sealing rings (front and rear) that prevent fluid from leaking out of the rear of the barrel during injection of fluid from the syringe. The rear sealing ring may not contact or seal the interior surface of the syringe barrel in an unloaded state. In the loaded state, when force is applied in the direction of the forward discharge end of the syringe, the plunger jacket assembly is moving forward relative to the syringe barrel, creating pressure on the jacket. This condition causes the rear seal to expand and contact and/or seal the interior surface of the syringe barrel.

As such, one aspect of the invention may include a plunger assembly for a syringe comprising a plunger body, and a jacket at least partially covering the plunger body, the jacket having a front sealing ring and a rear sealing ring, wherein the front sealing ring has a larger outer diameter than the rear sealing ring.

A second aspect of the invention may comprise a syringe assembly including a barrel having a generally cylindrical main body portion having an interior surface and an exterior surface, a closed forward end having a discharge aperture, and an open rear end; a plunger assembly located at least partially within the barrel, the plunger assembly including a plunger body and a jacket at least partially covering the plunger body; wherein, the plunger jacket comprises a forward-most sealing ring on a radially-outward surface and at least one auxiliary sealing ring on a radially-outward surface spaced rearwardly of the forward most sealing ring, and wherein the at least one auxiliary sealing ring forms a seal between the plunger assembly and the barrel only when a force is applied to the plunger assembly in the direction of the discharge aperture.

A third aspect of the invention may comprise a syringe plunger jacket having an axis, and comprising: a forward surface; an intermediate surface; and, a rear surface, wherein the jacket includes a recess extending forwardly from the rear surface and terminating at the intermediate surface, and wherein, a thickness as measured between the forward surface and intermediate surface increases as the distance from the axis increases.

In one embodiment of the present invention a plunger assembly for an associated syringe includes a plunger body, and a plunger jacket covering part or all of the plunger body. The plunger jacket may also include a front sealing ring and a rear sealing ring where an outer diameter of at least one of the front sealing ring and the rear sealing ring increases when force is applied to the jacket, of which said force may come from the pressure of ejecting fluid from an associated syringe.

In one aspect of the embodiments of the present invention the plunger assembly may include an axis coincident with the forward motion of travel for the plunger assembly, where the outer diameters of at least one of the front sealing ring and the rear sealing ring increase when axial force is applied to the jacket.

In another aspect of the embodiments of the present invention an outer diameter of at least one of the front sealing ring and the rear sealing ring increases in proportion to forces applied to the jacket for at least a range of pressures.

In another embodiment of the present invention, a syringe assembly for injecting associated fluid under pressure may include a barrel having a generally tubular or cylindrical main body portion where the body portion includes an interior surface, an exterior surface, and a body portion axis, which may be a longitudinal axis. One end of the body portion may be generally enclosed having a discharge aperture and the distal end of the body portion may be open. A plunger assembly is received at least partially within the barrel and may have a plunger assembly axis substantially coaxial to the body portion axis. The plunger assembly may be comprised of a plunger body and a plunger jacket at least partially covering the plunger body.

In one aspect of the embodiments of the present invention the plunger jacket includes at least a first sealing ring on a radially-outward surface where the sealing capability of the at least a first sealing ring increases responsive to opposing forces in the syringe assembly.

In another aspect of the embodiments of the present invention the outer diameter of the at least a first sealing ring and the inner diameter of the barrel comprise an interference fit where the interference fit increases responsive to opposing forces in the syringe assembly.

In yet another aspect of the embodiments of the present invention the plunger jacket may be fashioned from Chlorobutyl or from a blend of any or all of the following materials including but not limited to Chlorobutyl, Bromobutyl and Polyisoprene.

In another aspect of the embodiments of the present invention the plunger jacket may be fashioned from a thermoplastic elastomer (TPE), such as for example Santoprene™ as manufactured by Advanced Elastomer Systems or Kraton® as manufactures by Kraton Polymers. Although other types of thermoplastic polymers may also be used without departing from the intended scope of coverage of the embodiments of the present invention including but not limited to Polyvinyl Chloride (PVC) and Polyurethane.

Another embodiment of the present invention includes a method of injecting fluid into an animal comprising the steps of providing a syringe barrel having an axis, an interior surface, a forward discharge end, and an open rear end; providing a plunger assembly being substantially coaxial with the syringe barrel and received at least partially within the syringe barrel to enclose the open rear end of the syringe barrel, the plunger assembly including a plunger body and a plunger jacket at least partially covering the plunger body, wherein the plunger jacket comprises a forward circumferential sealing ring and a rearward circumferential sealing ring; filling the syringe with an associated liquid; and, actuating the plunger assembly to expel at least a portion of the associated liquid from the syringe under pressure thereby expanding at least one of the forward and rearward circumferential sealing rings thus preventing the associated liquid from leaking past the sealing rings.

In another aspect of the embodiments of the present invention the both the forward circumferential sealing ring and the rear circumferential sealing ring expand when the plunger assembly is driven forward.

In another aspect of the embodiments of the present invention the forward circumferential sealing ring and the rearward circumferential sealing ring have substantially the same outer diameter.

In yet another aspect of the embodiments of the present invention the forward circumferential sealing ring and the rearward circumferential sealing ring have substantially different outer diameters.

BRIEF SUMMARY OF THE DRAWINGS

FIG. 1 is a cross-sectional view of a preferred embodiment of a plunger jacket assembly, in accordance with an embodiment of the present invention.

FIG. 2 is a detailed view of a portion of the plunger jacket assembly of FIG. 1.

FIG. 3 is a front view of the jacket of FIG. 1.

FIG. 4 is a rear view of the jacket of FIG. 1.

FIG. 5 is another cross-sectional view of the jacket of FIG. 1, illustrated with angles α and β.

DETAILED DESCRIPTION OF THE DRAWINGS

Figure 6:
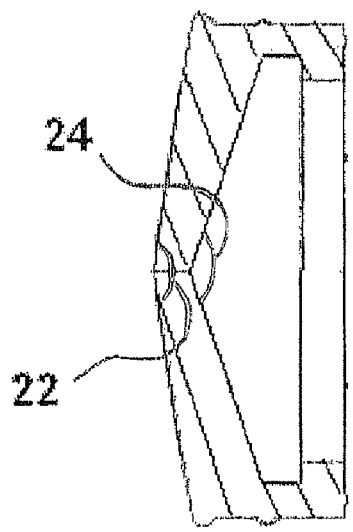
FIG. 6 is another cross-sectional view of the jacket of FIG. 1, illustrated with opening angles of the front surface and intermediate surface.
Figure 7:
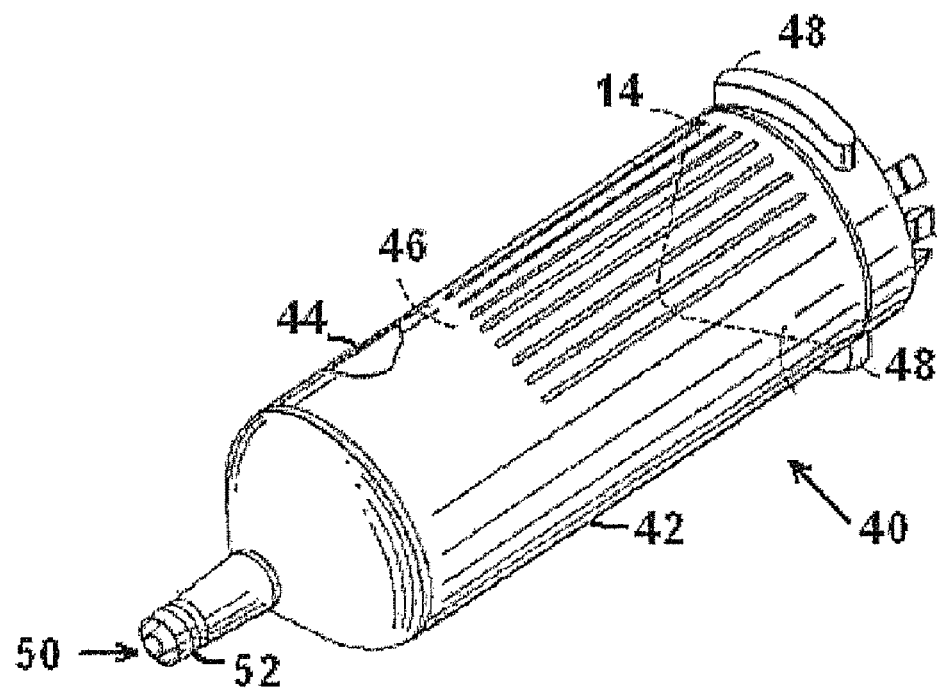
FIG. 7 is a perspective view of a syringe assembly.

The present invention will now be described in greater detail with reference to the appended drawings.

An embodiment of a syringe plunger-jacket assembly ("assembly") with expandable seal, generally identified by reference 10, is illustrated in FIGS. 1-7. The assembly 10 generally comprises a flexible jacket 12 and rigid plunger 20 (partially shown). The plunger 20 of the assembly 10 attaches to a drive ram of an injector, which moves the assembly forward to dispel contrast fluid from the syringe.

Jacket 12 may generally comprise a conical or frustoconical front surface 14, although the specific shape of front surface 14 may be dependent on the shape of the forward discharge end of the syringe barrel, i.e., the front surface 14 may be of the same angularity as the forward discharge end of the syringe. Syringe jacket 12 may be connected to any of a plurality of types and shapes of plungers 20, as chosen with sound judgment. For example, the plunger may have a plurality of opposed hook members that attach the plunger to the drive ram of the power injector. Alternatively, the plunger 20 may have a rearwardly extending projection that is attachable to the drive ram. Any other drive ram-plunger connections could be utilized without deviating from the scope of the embodiments of the present invention, as well. Alternatively, the plunger may comprise an elongated portion extending rearwardly from the syringe barrel, as is known in hand-actuated syringes and syringes for syringe pumps.

As illustrated in FIG. 1, the assembly 10 generally comprises a plurality of circumferential integral sealing rings 30, 32, which may be referred to as "seals." Although two seals or sealing rings are illustrated, it is contemplated that any number of sealing rings may be utilized. The forward-most seal 30 may contact the interior surface of the syringe barrel at all times as will be described below. However, rear expandable seal 32, or auxiliary seal or sealing ring may only contact the interior surface of a syringe barrel upon the forward movement of the assembly 10 within the syringe barrel during injection of fluid, i.e. a loaded condition or state. In a resting, or unloaded position or state, seal 32 may not contact the interior surface of a syringe barrel. As stated earlier, a seal 32 not contacting the syringe barrel eliminates the difficult-to-sterilize space typically between two seals. Alternatively, the auxiliary seal 32 may intermittently contact the interior surface of the barrel in the resting state, and form a seal with the barrel upon application of force $F_1$.

An exemplary configuration for the assembly 10 that enables seal 32 to expand during expulsion of fluid from the syringe is explained hereinafter. As illustrated in FIG. 1, the syringe jacket 12 may comprise front surface 14 and intermediate surface 18 that may contact a portion of the front of the plunger 20. Both the front surface 14 and intermediate surface 18 may comprise an apex 14' and 18'. Angle α is the angle formed between the front surface 14 and a line tangential to the apex 14' of the front of the jacket and perpendicular to bisecting line X. In comparison, β is the angle formed between the intermediate surface 18 and a line tangential to the apex 18' and perpendicular to bisecting line X.

Angle β may be larger than Angle α. In other words, as shown in FIG. 6, the opening angle 22, if the front and intermediate surfaces are conical-shaped, of the front cone 14 may be greater than the opening angle 24 of the intermediate cone 18. This differing angle results in a jacket 12 thickness that, as measured from front surface 14 to intermediate surface 18 in a direction parallel to bisecting line X, increases the farther radially outward that is measured. This different thickness is exemplified in FIG. 1, wherein length $\delta_1$ is less than $\delta_2$.

During an injection of fluid from the syringe, a force $F_1$ is applied by, for example, the drive ram of the injector to the rear end of the syringe plunger assembly 10 and in the direction of the forward discharge end of the syringe. Since the syringe barrel is filled with fluid, which may be saline or any contrast solution, the fluid creates an opposing axial force $F_2$ in a direction opposite of $F_1$. The assembly 10 therefore undergoes a compression as a result of the opposing axial force $F_2$. As a result, Force $F_3$ is generated, which causes the diameter of jacket 12 to increase. At the same time, seal 32 expands radially outward and contacts and/or seals against the interior surface of a syringe barrel increasing the interference between seal 32 and the barrel thus increasing the sealing capability of seal 32.

It is contemplated that the jacket 12 can be manufactured from any suitable flexible material. For example, chlorobutyl is a material that has been used in constructing syringe jackets 20; however, any suitable flexible material that has a moderate to low durometer may be appropriate. Materials with low durometers are potentially better suited for this application because softer materials tend to be change shape or deform more readily under pressure. However, alternatively, the material must be rigid enough to withstand major deformation.

It is contemplated that the gap between the interior of the syringe barrel and the expandable seal 32 may be on the order of 0.0010 inch, such that very little expansion is needed to form a useful seal. However, it is contemplated that any resting gap between the syringe barrel and the expandable seal 32 is contemplated, as long as the expandable seal contacts the interior of the syringe barrel during customary injection of fluid from the syringe. Without limiting the scope of the embodiments of the present invention, the particular application may have a gap ranging from 0.005" to 0.020." It is also contemplated that the expandable seal 32 may actually contact the interior of the syringe barrel intermittently, so long as sufficient discontinuous gaps exist to allow for sterilization of the area between the seals.

Figure 8:
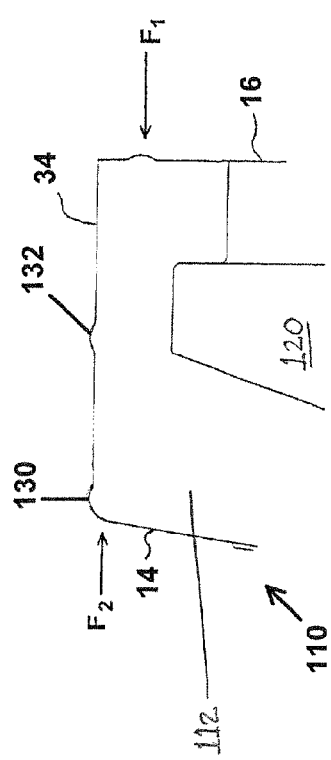
FIG. 8 is a detailed view of a portion of another embodiment of a plunger jacket.

Another embodiment of a syringe plunger-jacket assembly 110 is illustrated in FIG. 8. The assembly 110 generally comprises a flexible plunger jacket 112 and rigid plunger 120 (partially shown). The plunger jacket 112 may be similarly configured having an apex and differing wall thicknesses as described in a previous embodiment. The plunger 120 of the assembly 110 may likewise attach to a drive ram of an injector, which moves the assembly forward to dispel fluid from the syringe. The fluid used with the syringe may be saline solution or any contrast media chosen with sound judgment. The assembly 110 may also comprise one or more seals 130, 132, which may be expanding seals as described above.

With continued reference to FIG. 8, both seals 130, 132 of assembly 110 may contact the interior of the syringe barrel in a loaded and an unloaded state. For example, both seals 130, 132 may have substantially the same outer diameter. Other embodiments are contemplated where one of the seals 130, 132 may have a larger diameter than the other seal 132, 130. However in any case, both seals 130, 132 maintain contact with the interior surface of the barrel at all times. By contact it is meant that at least some portion, but possibly all, of the seal touches the interior surface of the barrel. Accordingly, the outer diameter of both of the seals 130, 132 may be substantially equivalent to or slightly larger than the interior diameter of the syringe barrel creating an interference fit between the seals 130, 132 and the barrel. However, neither of the seals 130, 132 may have tight contact with the interior surface of the barrel in an unloaded state. In one embodiment, the interference fit may range from about 0.0 mm to 1.25 mm. It is also contemplated that the interference fit may be negative, otherwise termed slip fit. More specifically, the interference may be in the range of 0.5 mm to 0.75 mm. However, any range of interference fit may be chosen as is appropriate for use with the embodiments of the present invention. It is noted here that the area between the seals 130, 132 may not be sterilized in the same manner as that of a previously described embodiment since the seals 130, 132 continuously contact the interior surface of the barrel thereby preventing gas from entering the region between the seals 130, 132. Other means of sterilization may be used such as, for example, gas channels fashioned in the barrel.

In the prior art, relatively tight contact with the syringe barrel in the unloaded state was needed to withstand the operating pressure of the injection process and resulted in chatter during actuation of the plunger through the barrel, of which the chatter is also a function of the material durometer. According to the embodiments of the present invention, in an unloaded state, a tight or snug fit between the seals 130, 132 and the barrel is not required because of the expanding seal configuration of the assembly 110 and the plunger jacket 112. As described above, resistance force from forward motion of the syringe plunger against the fluid translates through the plunger jacket 112 causing one or both of the seals 130, 132 to expand radially outward against the interior surface of the barrel. This increases the compression, between the seals 130, 132 and the barrel and thus increases the sealing capability of the plunger jacket 112 creating an effective seal against leakage of the fluid from the back of the syringe. It is noted that the seals 130, 132 may expand in proportion to the load or force applied to the plunger jacket 112. In this manner, the sealing capability of the seals 130, 132 may increase in the loaded state with respect to the unloaded state. As a result, chatter is reduced and operating pressures within the syringe are increased. Additionally, materials once thought unusable, may now be used to construct the plunger jacket 112 resulting in reduced manufacturing costs.

One type of material from which the plunger jackets may be constructed is a thermoset material, having relatively high tensile strength, such as for example Polyisoprene, that is more capable of withstanding deformation against larger injection pressures than other materials like, for example, Chlorobutyl. However, Polyisoprene may chatter during use especially as the interference fit between the sealing rings and the barrel increases. Conversely, while reducing chatter, Chlorobutyl is generally less capable of withstanding pressure with respect to that of Polyisoprene and accordingly has been used in lower pressure applications. Therefore sealing against higher injection pressures has typically required a higher tensile strength material and an increased interference between the plunger jacket seals, which may result in chatter. The embodiments of the present invention allow for materials having relatively lower tensile strength to be used in higher pressures applications since the plunger jacket automatically expands responsive to the load. Additionally, materials may now be blended in various proportions and formed to construct the plunger jacket 112 providing both an effective sealing against fluid leakage and reduced chatter in the barrel during use. By way of example, such material blends may include but are not limited to: Polyisoprene, Bromobutyl and Chlorobutyl.

The embodiments of the present invention further allow for other types of materials and processes to be used in manufacturing the plunger jackets. For example, thermoplastic materials may now be used to construct the plunger jacket 112. Typically, thermoplastic materials, under compression, may inelastically deform over time thereby diminishing their capability to withstand operating pressures during the injection process. However, according to the embodiments of the present invention, the plunger assembly may compensate for any deformation of material by expanding the seals 130, 132 thereby increasing the working pressure of the syringe. Accordingly, the plunger jacket 112 may be constructed from thermoplastic materials such as, but are not limited to: Santoprene, Kraton, PVC and polyurethane.

Further embodiments of syringe plunger-jacket assembly are also contemplated. For example, the jacket 112 may comprise a forward most seal 130 that continuously contacts the interior surface of the barrel and provides sufficient sealing in both a loaded and unloaded state. By loaded state it is meant that the plunger 120 is causing fluid to be expelled from the syringe under pressure. The rear seal 132 may be similar to seal 130, in that it also continuously contacts the interior surface of the barrel 42 in a loaded and unloaded state, but may only provide sufficient sealing in a loaded state via its expandability. In other words, one of the seals 130, 132, which may be the forward most seal 130, may have a greater interference fit than the other seal, which may be seal 132.

Figure 9:
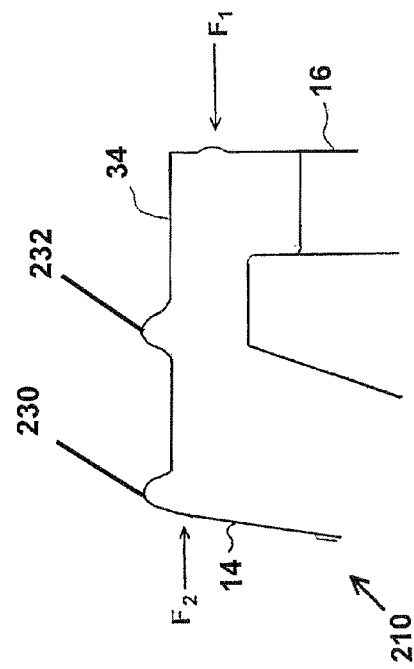
FIG. 9 is a detailed view of a portion of another embodiment of a plunger jacket.

FIG. 9 illustrates yet another embodiment 210 wherein seals 230, 232 are of larger diameter, i.e. having increased interference with the barrel, thereby providing sufficient sealing even in an unloaded state without the need to further expand. However, one or both of seals 230, 232 may further expand in a loaded state to additionally increase the sealing capability of the plunger jacket 112 relative to the interior surface 46 of the syringe barrel 42.

An exemplary embodiment of one syringe 40 that may be used with plunger/jacket assembly 10. Syringe 40 comprises barrel 42 having exterior surface 44 and interior surface 46. The syringe may have one or more retaining flanges 48 and a discharge aperture 50 and/or luer connection 52. In addition to or in lieu of the retaining flange(s), the syringe may have a continuous flange that encircles the syringe barrel 42.

The foregoing disclosure is illustrative of a present invention and is not to be construed as limiting thereof. Although one or more embodiments of the invention have been described, persons of ordinary skill in the art will readily appreciate that numerous modifications could be made without departing from the scope and spirit of the disclosed invention. As such, it should be understood that all such modifications are intended to be included within the scope of this invention. During the description and the drawings illustrate one or more exemplary embodiments of the present invention and are not to be construed as limiting.

What is claimed is:

1. A plunger jacket for an associated syringe having a plunger defining a central axis, comprising:
    a plunger jacket body at least partially covering the plunger and having a front conical surface forming a first apex and an intermediate conical surface forming a second apex wherein said first apex and said second apex lie on the central axis, wherein the front conical surface defines a first opening angle with respect to the central axis and the intermediate conical surface defines a second opening angle with respect to the central axis, wherein said first opening angle is greater than said second opening angle such that said front conical surface and said intermediate conical surface form a front wall of the plunger jacket having a thickness that increases in the axial direction as said front conical surface and said intermediate conical surface extend radially outward;
    wherein the plunger jacket has a forwardmost sealing ring and a rearwardmost sealing ring each protruding from the plunger body in a resting state, wherein said rearwardmost sealing ring protrudes from said plunger body near the intersection of a line corresponding to said intermediate conical surface and an exterior of the plunger body, wherein a resultant force extending generally along said line of said intermediate conical surface causes an outer diameter of only the rearwardmost sealing ring to increase when said plunger jacket is driven forward; and,
    wherein an outer diameter of the forward-most sealing ring in the resting state is substantially the same as the outer diameter of the rearwardmost sealing ring in the resting state, wherein said forwardmost sealing ring and said rearward-most sealing ring are separated by a space, said forwardmost sealing ring being adapted to sealingly engage the syringe in the resting state, while said space is unsealed at said rearward-most sealing ring when in the resting state to allow sterilization fluid to flow into the space between said forwardmost sealing ring and said rearwardmost sealing ring when the plunger jacket is in said resting state.

2. A syringe assembly for injecting an associated fluid under pressure, comprising:
    a barrel having a generally tubular main body portion, the body portion having an interior surface and a discharge aperture fashioned in an enclosed forward end, the body portion having an open rear end;
    a plunger assembly received at least partially within the body portion for expelling associated fluid through the discharge aperture, the plunger assembly including:
        a plunger body having a central axis and,
        a plunger jacket at least partially covering the plunger body, wherein the plunger jacket includes first and second sealing rings each contacting the interior surface of the barrel in both a loaded state and a resting state; and
    wherein the plunger jacket includes front and intermediate surfaces each forming apices coaxial with the central axis, wherein the front surface is linearly sloped defining a first angle with respect to the central axis and the intermediate surface is linearly sloped defining a second angle with respect to the central axis for expanding, wherein said first angle is greater than said second angle such that a thickness of said plunger jacket between said front surface and said intermediate surfaces increases rearwardly as said front surface and said intermediate surface extend radially outward from the central axis, wherein said second sealing ring extends outward from said plunger jacket near the intersection of a line corresponding to said intermediate surface and an exterior of the plunger jacket; and,
    wherein a resultant force is formed along said line corresponding to said intermediate surface causing the second seal to expand radially outward without expanding the diameter of said first seal such that the sealing capability of the second sealing ring increases responsive to expelling associated fluid through the discharge aperture.

3. The syringe assembly of claim 2, wherein an outer diameter of the second sealing ring and the interior surface of the body portion comprise an interference fit, and, wherein the interference fit increases responsive to pressure generated in the body portion from expelling the associated fluid.

4. The syringe assembly of claim 3, wherein at least a portion of the outer diameter of the plunger jacket is fashioned from a thermoset material.

5. The syringe assembly of claim 3, wherein the plunger jacket is fashioned from a thermoplastic material.

6. The syringe assembly of claim 3, wherein the second sealing ring intermittently contacts the barrel in the resting state forming a discontinuous gap between the second sealing ring and the barrel.

7. The plunger jacket as defined in claim 1, wherein the front conical surface defines a circumferential edge, and wherein the front sealing ring protrudes from the plunger jacket body at the circumferential edge.

8. The syringe assembly as defined in claim 2, wherein the front and intermediate surfaces are conically shaped.

* * * * *